(12) United States Patent
Groenhuis et al.

(10) Patent No.: US 7,247,938 B2
(45) Date of Patent: Jul. 24, 2007

(54) CARRIER, METHOD OF MANUFACTURING A CARRIER AND AN ELECTRONIC DEVICE

(75) Inventors: Roelf Anco Jacob Groenhuis, Nijmegen (NL); Paul Dijkstra, Nijmegen (NL); Cornelis Gerardus Schriks, Nijmegen (NL); Peter Wilhelmus Maria Van De Water, Nijmegen (NL)

(73) Assignee: NXP B.V., Eindhoven (NL)

( * ) Notice: Subject to any disclaimer, the term of this patent is extended or adjusted under 35 U.S.C. 154(b) by 260 days.

(21) Appl. No.: 10/510,588

(22) PCT Filed: Apr. 10, 2003

(86) PCT No.: PCT/IB03/01299

§ 371 (c)(1),
(2), (4) Date: Oct. 8, 2004

(87) PCT Pub. No.: WO03/085728

PCT Pub. Date: Oct. 16, 2003

(65) Prior Publication Data

US 2005/0153483 A1 Jul. 14, 2005

(30) Foreign Application Priority Data

Apr. 11, 2002 (EP) ................... 02076426
Oct. 30, 2002 (EP) ................... 02079544

(51) Int. Cl.
*H01L 23/04* (2006.01)
(52) U.S. Cl. .................. 257/699; 257/E23.06
(58) Field of Classification Search ............... 257/699
See application file for complete search history.

(56) References Cited

U.S. PATENT DOCUMENTS

| 6,306,685 B1 | 10/2001 | Liu et al. |
| 6,351,025 B1 | 2/2002 | Ohsawa et al. |
| 6,451,627 B1 * | 9/2002 | Coffman ............... 438/111 |

* cited by examiner

*Primary Examiner*—David A. Zameke
(74) *Attorney, Agent, or Firm*—Peter Zawilski

(57) ABSTRACT

The carrier (30) comprises a first etch mask (14), a first metal layer (11), an intermediate layer (12), a second metal layer (13) and a second etch mask (17). Both the first and the second etch mask (14, 17) can be provided in one step by means of electrochemical plating. After the first metal layer (11) and the intermediate layer (12) have been patterned through the first etch mask (14), an electric element (20) can be suitably attached to the carrier (30) using conductive means. In this patterning operation, the intermediate layer (12) is etched further so as to create underetching below the first metal layer (11). After the provision of an encapsulation (40), the second metal layer (13) is patterned through the second etch mask (17). In this manner, a solderable device (10) is obtained without a photolithographic step during the assembly process.

10 Claims, 3 Drawing Sheets

CARRIER, METHOD OF MANUFACTURING A CARRIER AND AN ELECTRONIC DEVICE

The invention relates to a method of manufacturing an electronic device provided with an electric element and a carrier with a first side and a second side, comprising a stack of a first patterned metal layer, a patterned intermediate layer and a second metal layer, which method comprises the steps of:

placing an electric element on the first side of the carrier, contacts of the electric element being electroconductively connected to the first metal layer; and providing an envelope around the electric element.

The invention further relates to a carrier having a first and a second side, comprising a stack of a first metal layer, an intermediate layer and a second metal layer.

The invention also relates to a method of manufacturing a carrier with a first side and an opposite second side, comprising the steps of:

providing a stack of a first metal layer, an intermediate layer and a second metal layer, wherein the first and the second metal layer are electroconductively interconnected, and wherein the first metal layer is situated on the first side; and patterning the first metal layer in accordance with a desired pattern.

Such a carrier and such a method of manufacturing an electronic device comprising the carrier are known from EP-A 1.160.858. The known carrier is a carrier of Al, Cu, Fe—Ni alloy or of a stack of Cu—Al or Al—Cu—Al. The carrier is provided on the first side with the desired pattern and with a conductive layer of at least one of the metals Ni, Au, Ag and Pd. In the manufacturing process of the device, after placing a semiconductor element and providing the envelope, the part of the carrier wherein the pattern is not provided is removed. Subsequently, a mask is photolithographically provided on the second side of the carrier, after which contact surfaces or guide pins are formed.

A drawback of the known method resides in that a photolithographic step is required after assembly of the electric element. This means that this step must be carried out in the assembly plant, which is undesirable on account of customarily prevailing conditions in such a plant.

Therefore it is a first object of the invention to provide a method of manufacturing an electronic device of the type mentioned in the opening paragraph, wherein no photolithographic step is required after the placement of the electric element, which method nonetheless yields a compact and sufficiently sturdy device.

The first object is achieved in that the carrier comprises an etch mask on the second side, and the first metal layer of said carrier is electroconductively connected to the second metal layer and has parts projecting with respect to the intermediate layer. After the provision of the envelope, which preferably envelops the electric element entirely, the second metal layer is etched from the second side of the carrier in accordance with the pattern defined by the etch mask.

In the method in accordance with the invention, the second metal layer of the carrier is not removed completely, but is rather used to define therein the contact surfaces and any other patterns. Advantageously, the pattern is fixed by means of the etch mask, which has been provided before the assembly process.

The fact that the second layer is not removed means that the carrier is attached to the envelope. To make sure that the carrier is properly attached to the envelope, the first metal layer of the carrier is mechanically anchored in the envelope.

For this purpose, the first metal layer and the intermediate layer are patterned such that the first metal layer has parts projecting with respect to the intermediate layer. The parts thus project in a direction parallel to the sides of the carrier. The intermediate layer is patterned preferably by means of etching, an etchant being used that is selective with respect to the first metal layer. This results in a degree of underetching of the first metal layer, which is found to be sufficient for mechanical anchoring.

The build-up of the carrier is such that the thickness of each of the constituent layers can be kept down. After all, the mechanical stability is not determined by the first metal layer but by the carrier as a whole. As the resolution of the pattern is also determined by the layer thickness, the invention enables a carrier with a first metal layer having a very high resolution to be obtained. This effect enables further miniaturization as well as a specific definition of tracks, as is desirable for fine-pitch and high-frequency applications.

An advantage of the method is that it enables a great variety of electronic devices to be manufactured. In particular, the method is suited for semiconductor devices, but also other devices with sensors, micro-electromechanical system (MEMS) elements or display devices can be manufactured by means of said method.

A first group of devices are compact semiconductor devices comprising several to approximately forty contact surfaces. This is the case, in particular, because high-resolution patterns can be defined in the first metal layer, while the second metal layer may comprise contact surfaces which are spaced apart sufficiently to be able to apply solder to them using standard equipment.

A second group of devices includes semiconductor devices comprising more than one electric element, which electric elements must be interconnected. As the first and the second metal layer are patterned independently, interconnect tracks from a first to a second element can be defined in the first metal layer. These interconnect tracks are absent from the pattern in the second metal layer. Thus the risk of undesirable contact between such interconnect tracks and a circuit board during the provision of solder on the second side of the carrier is absent.

A particularly advantageous example of such an application is found in a device comprising first of all an integrated circuit and, in addition, one or more diodes for protection purposes as the elements. For the diodes use can be made, in this case, of, for example, diodes with SMD contacts.

In a further embodiment of the method, the electric element is situated in a cavity in a substrate, said cavity being filled when the envelope is provided around the element. This embodiment is particularly advantageous for devices operating at high powers, because said embodiment enables a heat conductive layer to be applied to the bottom of the cavity. The embodiment is also suitable for modules, in particular modules with high-power elements, such as amplifiers. Thus, various components can be accommodated in different cavities and contacted and conductively interconnected via the three-layer or multilayer carrier. It is also possible to define contact surfaces in the first metal layer for contacting conductors on the substrate.

In a favorable embodiment, the etch mask has an adhesive layer for solder, which adhesive layer is also present on the first side of the carrier. A first advantage of this embodiment is that the adhesive layer can be deposited during the manufacture of the carrier. A second advantage is that the adhesive layer can also be used as an etch mask. A third advantage is that the adhesive layer can be provided on the first side and on the second side of the carrier in a single process.

Patterning of the first metal layer and the intermediate layer can take place during the manufacture of the carrier as well as during the assembly process, prior to the placement of the electric element. If the metal layers are very thin, generally less than approximately 30 μm, it may be favorable if patterning of these layers forms part of the assembly process. In this case, the risk of fracture or deformation of the carrier during transport is absent. Also the risk that the holes in the first metal layer and the intermediate layer are contaminated with dust or otherwise is absent. Such contamination may weaken the adhesion of the carrier to the envelope.

It is also favorable if, prior to placing the electric element, a liquid or liquefiable layer is applied to the first side of the carrier. If a liquefiable layer is used, a heating step is carried out after the electric element has been placed to liquefy said liquefiable layer. By using such a layer, which is described in the non-prepublished patent application EP 02077228.1 (PHNL020471) deformation of the solder or metal bump is counteracted. The use of such metal or solder bumps is known and has a favorable effect on the process of interconnecting the element and the first metal layer. Alternatively, for example a conductive adhesive or a number of bonding wires may be used to establish said connection.

The method in accordance with the invention can be advantageously applied particularly in combination with the carrier in accordance with the invention.

It is a second object of the invention to provide a carrier of the type mentioned in the opening paragraph, by means of which a compact and nevertheless sturdy electronic device can be manufactured without a photolithographic step being required after the assembly of an electric element on the carrier.

Said second object is achieved in that the carrier comprises a stack of a first etch mask, a first metal layer, an intermediate layer, a second metal layer and a second etch mask, the first etch mask being situated on the first side of the carrier, and the second etch mask being situated on the second side of the carrier.

The carrier in accordance with the invention differs from the known carrier in that an etch mask is present on the first side as well as on the second side. By virtue thereof, it is possible to define independent patterns in the first and the second metal layer.

In a favorable embodiment, at least the second etch mask comprises an adhesive layer for solder. Examples of such adhesive layers are, inter alia, layers containing at least one of the metals Ag, Pd, Au and Ni. Alternatively, for eutectic soldering use can be made of an alloy with Au and Ge, such as Ti—Ni—Au—Ge. The etch mask may be composed of the adhesive layers, but alternatively additional layers may be present such as, for example, a photoresist. Such a photoresist has the advantage that it forms a protective layer for the adhesive layer during the transport of the carrier. It has been found that the second metal layer, for example of Cu, can be etched at a sufficiently good etching rate and etching selectivity with respect to this adhesive layer. For the etchant use is made, for example, of a solution of $Na_2S_2O_8/H_2SO_4$. The adhesive layer can be advantageously provided in accordance with a pattern by means of a plating process, such as electroplating.

In a further embodiment, also the first etch mask has an adhesive layer for solder, which adhesive layer has the same composition as the adhesive layer in the second etch mask.

Such a carrier can be obtained in a simple manner by immersing the entire carrier in a bath. In this process, the adhesive layer is deposited on the first and the second side of the carrier at locations where said carrier is uncovered. An additional advantage of the use of the same adhesive layer resides in that the number of etchants is limited. By virtue of the intermediate layer, the second metal layer will not be attacked during etching the first metal layer.

In a particularly advantageous embodiment, a multilayer having Ni, Pd and Au sub-layers can be used as the adhesive layer. This layer is suitable for placing the electric element and for electroconductively connecting the electric element, and it is also suitable for use as an etch mask and for soldering the electronic device.

The intermediate layer of the carrier is most preferably made from a material that can be selectively etched with respect to the first metal layer. Preferably use is made of a metal, which has the advantage that the intermediate layer does not have to be separately patterned. Examples of suitable metals include Al, alloys of Al, FeNi, FeCrNi and stainless steel. Preferably it has a thickness between 10 and 100 μm, more preferably between 20 and 50 μm. Preferably the first and third metal layer have a thickness between 5 and 50 μm, by further preference between 10 and 40 μm.

It is particularly favorable if a metal that serves as a solder stop is used for the intermediate layer, in particular a metal or alloy which is electroconductive but not subject to moistening by solder. Particularly favorable results are achieved when use is made of Al or an alloy of Al as the intermediate layer, and first and second metal layers of Cu. Alloys of Al that can be used comprise inter alia $Al_xSi_{1-x}$, $Al_xCu_{1-x}$ and $Al_xGe_{1-x}$, wherein preferably $0.5 \leq x \leq 0.99$.

Alternatively, the intermediate layer may contain an insulating material, in which case conductive connections are provided in said intermediate layer. Such conductive connections can be obtained, for example, by applying a conductive layer from a solution after patterning the intermediate layer, and reinforcing said conductive layer by means of a plating process. Examples of conductive layers that can be applied from solution include inter alia a layer of a conductive polymer such as polyethylene dioxythiophene (PEDOT) and a silver layer formed by means of sol-gel processing. The intermediate layer may alternatively comprise a stack of sub-layers.

A third object of the invention is to provide a method of manufacturing a carrier, by means of which layers having a desired pattern can be provided on two opposite sides in a limited number of steps:

providing a stack of a first metal layer, an intermediate layer and a second metal layer, wherein the first and the second metal layer are electroconductively interconnected, and wherein the intermediate layer comprises a material that can be selectively etched with respect to the first metal layer, and wherein the first metal layer is situated on the first side;

applying and patterning a photosensitive layer on the second side; and electrochemically providing an adhesive layer for solder on the first and the second side.

In the method in accordance with the invention, the adhesive layers are electrochemically provided on both sides of the carrier in a single step. In this manner a carrier having the desired functionality is obtained in a simple manner. If the carrier is used, the adhesive layer on the second side can serve as an etch mask.

In a favorable embodiment, the adhesive layer is applied to the first side after a photosensitive layer has been applied to said first side in accordance with the pattern desired for the first metal layer. This photosensitive layer is removed after the adhesive layer has been applied, after which the adhesive layer serves as an etch mask for the first metal layer. This metal layer is patterned by means of etching, after which the intermediate layer is patterned by etching using an etchant which is selective with respect to the first and the third metal layer. In this process, underetching occurs with respect to the first metal layer. For the photosensitive layer use is made of, for example, SP2029-1 by Shipley. After curing, this layer exhibits sufficient mechanical stability. Thus, during applying the photosensitive layer to the second side, the carrier can be allowed to rest, without any problem, on the developed and patterned photosensitive layer on the first side.

Favorable adhesive layers comprise one or more metals selected from the group composed of Ni, Pd, Ag and Au. The metals can be present as sub-layers but also as an alloy.

These and other aspects of the carrier and the methods of manufacturing the carrier and the electronic device in accordance with the invention are apparent from and will be elucidated with reference to the embodiment(s) described hereinafter.

Figure 1:
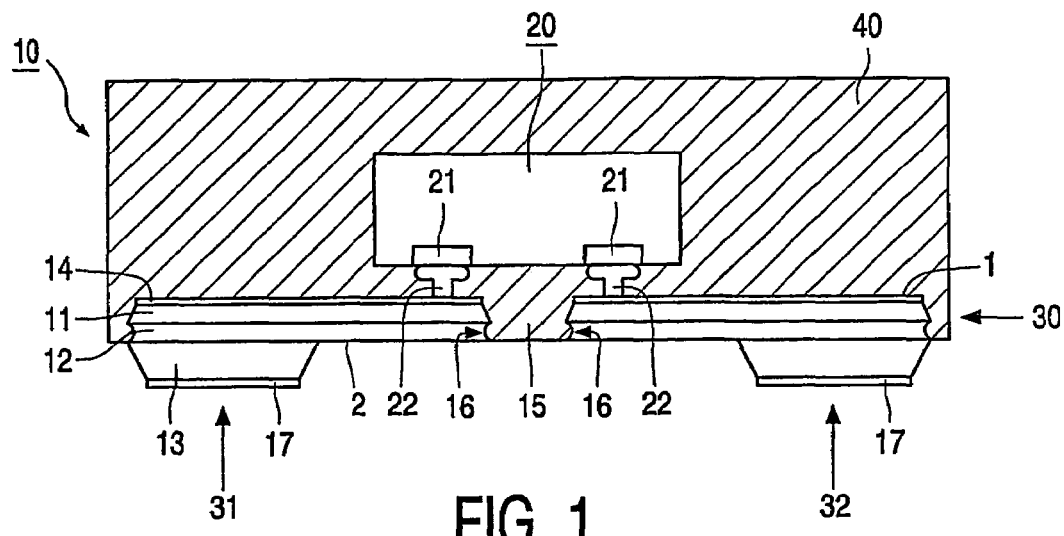
FIG. 1 is a diagrammatic cross-sectional view of a first embodiment of the electronic device.

The figures are not drawn to scale. Like reference numerals refer to like parts. Alternative embodiments are possible within the scope of protection of the appended claims.

Figure 2:
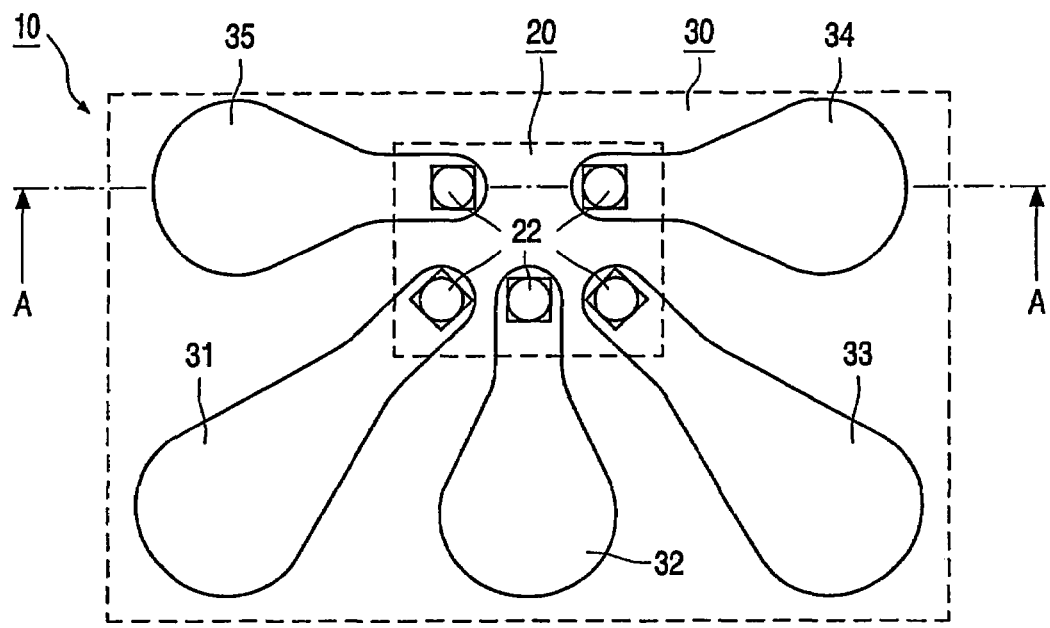
FIG. 2 is a diagrammatic plan view of the first embodiment.

FIG. 1 is a diagrammatic cross-sectional view of a first embodiment of an electronic device 10. In this case, said electronic device is a semi-discrete semiconductor device with five contacts. This however is by no means essential. FIG. 2 is a diagrammatic plan view of the first embodiment, wherein the line A-A indicates the cross-section of FIG. 1. The semiconductor device comprises a carrier 30 with a first metal layer 11, an intermediate layer 12 and a second metal layer 13. In this example, the first and the second metal layer 11, 13 comprise Cu, and the intermediate layer comprises $Al_{0.99}Si_{0.01}$. Furthermore, the carrier 30 comprises a first etch mask 14 and a second etch mask 17. The first and the second etch mask 14, 17 each comprise an adhesive layer of NiPdAu. The carrier 30 is patterned from the first side by means of the first etch mask 14, thereby forming apertures 15 and connection conductors 31-35. For this purpose use is made of an etching process wherein first the first metal layer 11 is etched and subsequently the intermediate layer 12 is etched, thereby forming recesses 16 in the side faces of the connection conductors 31-35. Subsequently, the semiconductor element 20 having connection regions 21 is connected to the connection conductors 31-35 by connection means 22, in this case bumps of Au. For this purpose, use is made of a flip-chip technique. Subsequently the envelope 40 is provided, resulting in the formation of a mechanical anchor since the envelope 40 extends into the recesses 16 of the carrier. Subsequently, the second metal layer 13 is patterned by means of the second etch mask 17. This is achieved by placing the device in an etch bath that selectively removes the second metal layer 13 with respect to the intermediate layer as well as with respect to the second etch mask 17. The apertures 15 are subsequently also used to separate the semiconductor devices 10. This has the additional advantage that the mechanical anchoring substantially encapsulates the connection conductors 31-35, i.e. not only at the location of the semiconductor element 20 but also beyond said element. The size of the semiconductor device 10 is, for example, approximately 1 by 1 mm. The opening 15 has a width of, for example, 40-100 μm. The thicknesses of the first metal layer 11, the intermediate layer 12 and the second metal layer 13 were chosen to be, respectively, 30 μm, 40 μm and 30 μm.

Figure 3:
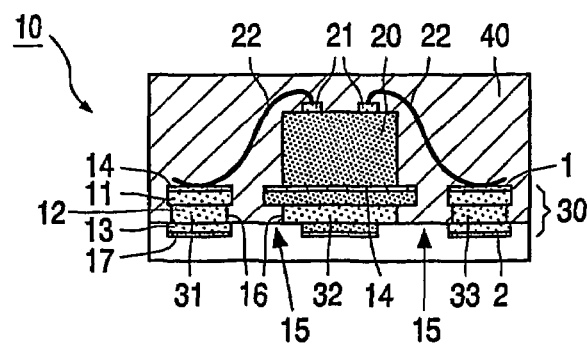
FIG. 3 is a diagrammatic cross-sectional view of a second embodiment of the electronic device.

FIG. 3 is a diagrammatic cross-sectional view of a second embodiment of the device 10 in accordance with the invention, in this case a semiconductor device. This device 10 comprises a semiconductor element 20 that is present on a carrier 30. Said carrier 30 has a first side 1 and a second side 2 and comprises a number of connection conductors 31, 32, 33. Said connection conductors 31, 32, 33 having side faces are mutually isolated by apertures 15. Between the connection conductors 31, 32, 33 and connection regions 21 in the semiconductor element 20 there are connection means, in this case bonding wires 22. In this example, the semiconductor element 20 is attached to the first side 1 of the carrier 30 by means of an adhesive layer 23. The semiconductor element 20 and the bonding wires 22 are encapsulated by an envelope 40. This envelope 40 extends into the apertures 15 of the carrier 30.

In accordance with the invention, recesses 16 are present in the side faces of the connection conductors 31, 32, 33. These recesses 16 are filled with the envelope 40, as a result of which the first layer 31 is partly clamped by the envelope 40. This ensures that the envelope 40 is mechanically anchored in the carrier 30, leading to excellent adhesion and mechanical strength. In this case, adhesion-improving means do not have to be provided on the first side 1 of the carrier. The first side 1 can also be optimized for the placement of the semiconductor element 20 and the bonding wires 22.

In accordance with a further feature of the invention, a second adhesive layer 17 is present on the second side of the carrier 30, and the second metal layer 13 has the same pattern as the second adhesive layer 17. As a result, the device can be manufactured without a photolithographic step being necessary during assembling electric element 20 on the carrier 30. The second adhesive layer 17 also serves as an adhesive layer for solder, which can be used to place the device 10 on a printed circuit board.

In this embodiment, the carrier 30 is composed of a first metal layer 11, an intermediate layer 12 and a second metal layer 13. The first metal layer 11 and the second metal layer 13 comprise mainly copper, and the intermediate layer 12 comprises mainly aluminum. The recesses 16 in the second layer 12 are formed by means of etching, as will be explained with reference to FIGS. 4-9. The first and second adhesive layers comprise NiPdAu or NiPd. As will be understood by persons skilled in the art, the adhesive layers 14, 17 may also comprise a different suitable material. Through the openings 15 which extend as far as the second side of the carrier 30, the second metal layer 13 is patterned so as to form contact surfaces, in this case for a bipolar transistor. The connection conductor 32 is connected to ground and serves as a heat sink.

Figure 4:
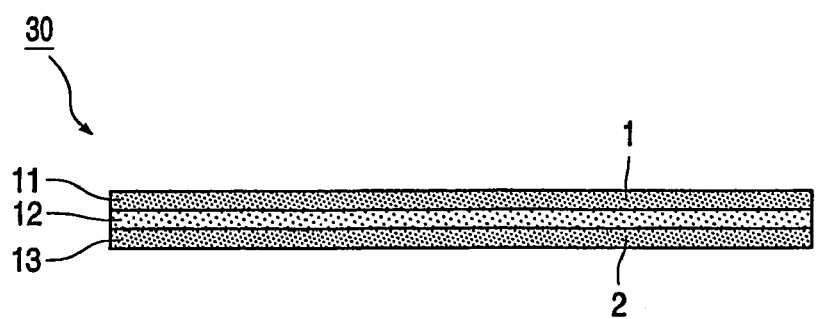
FIGS. 4-9 show steps in the methods of manufacturing the carrier and the electronic device as shown in FIG. 3.
Figure 5:
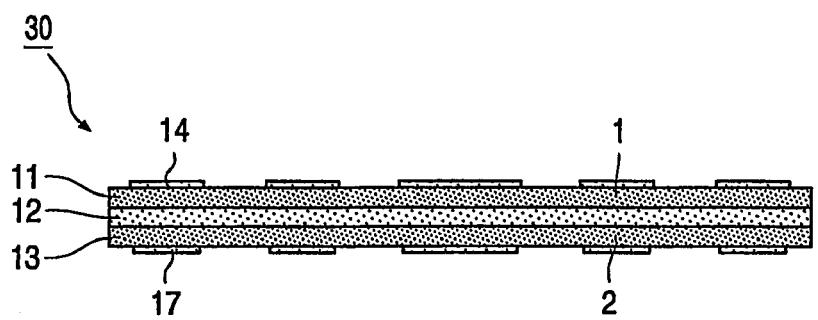
Figure 6:
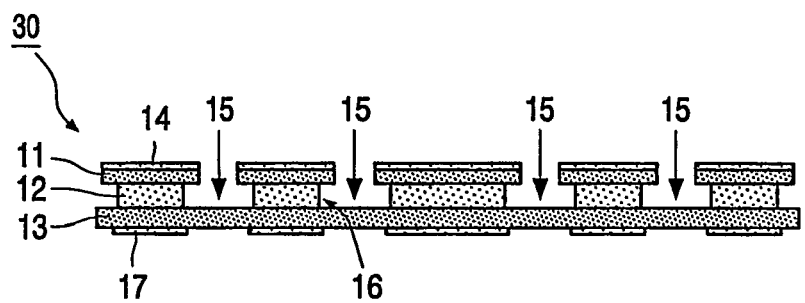

FIGS. 4-12 show various steps in the methods in accordance with the invention, which lead to the second embodiment as shown in FIG. 1. FIGS. 4 and 5 relate to the method of manufacturing the carrier 30. The FIGS. 7, 8 and 9 relate to the method of manufacturing the device 10. FIG. 6 relates to two steps which can be carried out in the manufacture of the carrier 30 as well as in the manufacture of the device 10.

The methods shown here have the advantage that they can be carried out without a lithographic step being required after the provision of the envelope, while at the same time the adhesion to the envelope 40 is very good and the carrier 30 does not disintegrate before the enveloping step.

FIG. 4 shows the carrier 30 after a first step wherein a first metal layer 11 of Cu, an intermediate layer 12 of Al and a second metal layer 13 of Cu are adhered to each other. It is possible to use the intermediate layer 12 as the starting layer, and provide a layer of Cu on either side thereof. Alternatively, the carrier 30 may be formed by rolling together the layers 11, 12, 13, which technique is customarily used to form bilayers. Said rolling process can also take place in two steps. It is also possible that eventually a four-layer or multilayer carrier is formed. The layers 11, 12, 13 had a thickness of 70 μm in a first experiment. The thickness may vary, however, between 10 μm and 1.0 mm, and the layers 11-13 do not have to be equal in thickness. If the first metal layer 11 is comparatively thin, it is preferably made of a material having a great mechanical strength and rigidity, such as a nickel-iron alloy. In combination with said material, copper can be used as the material for the intermediate layer 12. A heat treatment may be done to improve the adhesion between the layers 11, 12, 13, if this should be necessary.

FIG. 5 shows the carrier 30 after a first etch mask 14 is provided on the first side 1, and a second etch mask 17 is provided on the second side 2. Said etch masks are provided by applying a photoresist (for example SP2029-1 by Shipley) to successively the first side 1 and the second side 2 and subsequently patterning said photoresist. In the patterning operation, the photomask is also cured. The first side 1 and the second side 2 have different patterns. After the photoresist on the first side 1 has been patterned, the carrier 30 is turned upside down, after which the photoresist is applied to the second side. Subsequently, Ni, Pd and Au are successively provided on the carrier. Ag is an alternative. After this, the carrier is ready. Preferably the photoresist is removed. However, the photoresist may also be maintained to serve as a protective layer.

FIG. 6 shows the carrier 30 after the following steps have been carried out. First of all, the photoresist used as a protective layer is removed. Subsequently the carrier 30 is treated in a number of baths; first the carrier 30 is etched in a bath of a $Na_2S_2O_4/H_2SO_4$ solution for 5 to 10 minutes at 45° C. As a result, the first metal layer is etched in accordance with a pattern defined by the first etch mask 14. Next the carrier 30 is treated in a bath of a concentrated solution of KOH for 3 minutes, as a result of which the intermediate layer 12 of Al is etched and recesses 16 are formed. After said three minutes the recesses had a width of 70 μm. A width of 10-20 μm is sufficient to obtain the desired mechanical anchoring. Such a width additionally has the advantage that the connection conductors can be miniaturized; for a connection conductor having a width of approximately 100 μm, wherein recesses 16 are formed at two side faces, the width of the recess is approximately 30 μm at the most.

Figure 7:
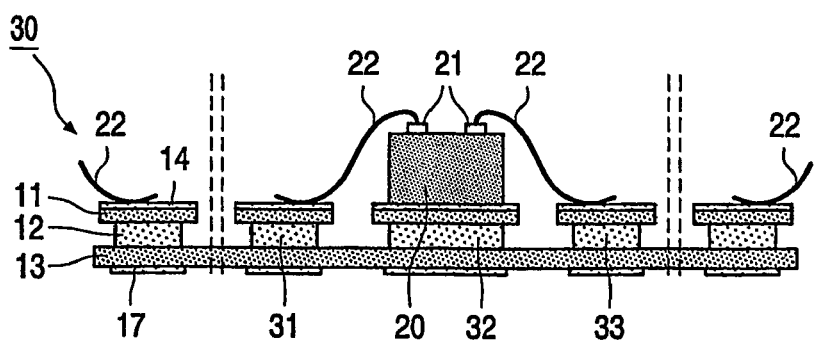

FIG. 7 shows the carrier 30 after semiconductor elements 20 are attached to the carrier 30 and bonding wires 22 are provided between the connection regions 21 of the semiconductor elements 20 and the connection conductors 31, 33. Although only a single element 20 is shown, in practice a large number of elements are placed on one carrier 30, which will only be separated at a later stage.

Figure 8:
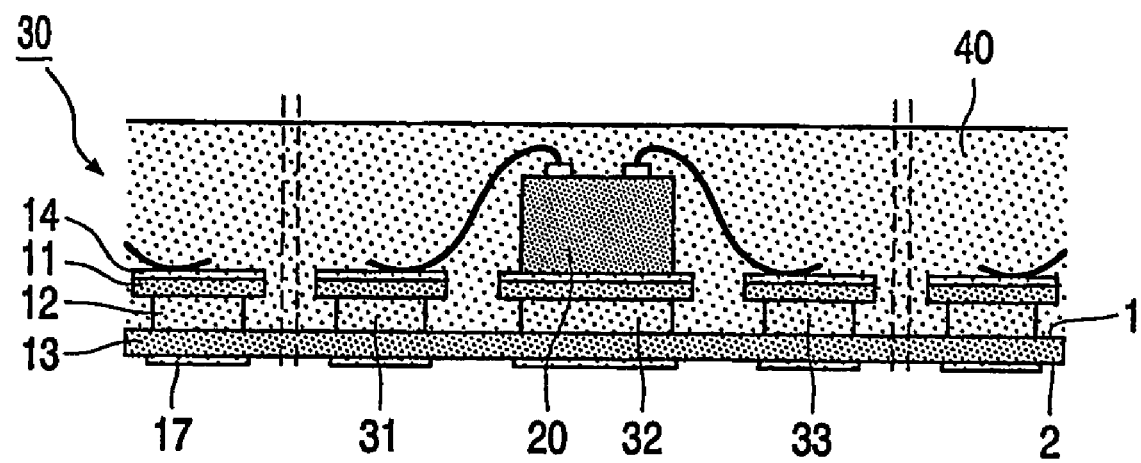

FIG. 8 shows the carrier 30 after the envelope 40 has been provided on the first side 1. As the second metal layer 13 is not patterned yet, it serves as a barrier for the enveloping material. This material also enters the recesses 16, thereby causing the first metal layer 11 to be mechanically anchored in the envelope 40. The envelope 40 is provided at the level of the carrier. The adhesion between the envelope 40 and the carrier can be further improved by providing the first metal layer 11 and hence the etch mask 14 with a rough surface. At the locations where the wire bonds must be provided, however, this surface is planarized by a planarization step. This planarization step is carried out already before the carrier 30 is provided with the etch mask 14, 17. For the planarization step use can be made, for example, of a roller that smoothens the outermost surface, while leaving open some holes below this surface for the adhesion of the envelope.

Figure 9:
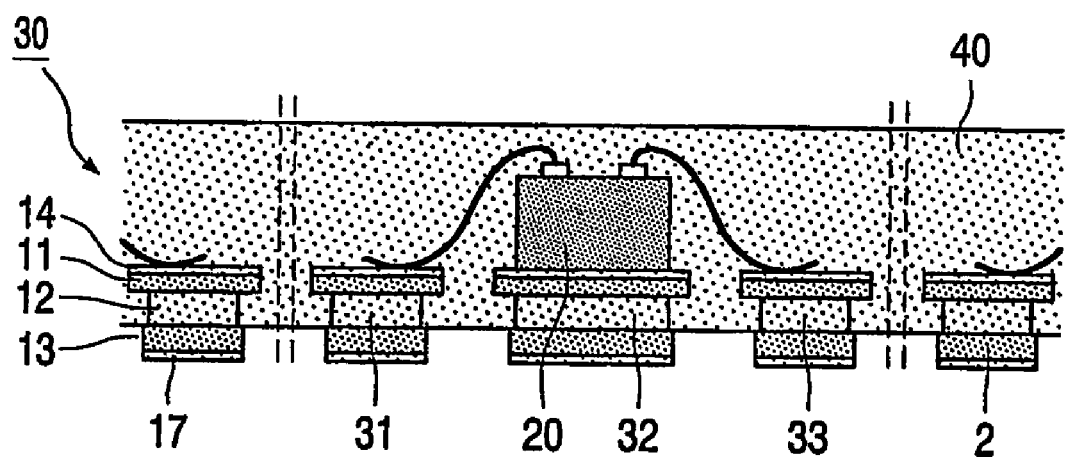

FIG. 9 shows the carrier 30 with element 20 and envelope 40 after the second metal layer 13 has been patterned. This is achieved by placing or immersing the carrier 30 with the second side 2 in a bath of $Na_2S_2O_4/H_2SO_4$ solution for 5 to 10 minutes at 45° C. The pattern is chosen to be such that separation lanes are defined wherein the carrier 30 is removed entirely. After cutting the envelope 40 along these separation lanes, for example by means of sawing, a finished device 10 is obtained.

The invention claimed is:

1. An electronic device comprising a carrier having, between a first side and an opposite second side,
   a first etch mask,
   a first patterned metal layer,
   a patterned intermediate layer,
   a second patterned metal layer and
   a second etch mask for use of etching of the second metal layer,
      wherein the first and second etch mask each have an adhesive layer for solder,
      wherein the first patterned metal layer is electroconductively connected to a first electric element and to the second metal layer, and the first patterned metal layer further includes parts projecting with respect to the intermediate layer, the projecting parts of the first metal layer are anchored in an envelope in which the first electric element is present on the first side of the carrier,
      wherein contacts of the electric element are electroconductively connected to the first metal layer, and
      wherein the first electric element and a second electric element are interconnected by an interconnect track that is defined in the first metal layer, while a corresponding interconnect track is absent in the second metal layer.

2. The electronic device as recited in claim 1, wherein the first and the second etch mask comprise an adhesive layer for solder.

3. The electronic device as recited in claim 2, wherein the adhesive layer for solder comprises a material selected from the group composed of Ag, NiPd, NiPdAu.

4. The electronic device as recited in claim 1, wherein the intermediate layer comprises an electroconductive material that can suitably be used as a solder stop.

5. The electronic device as recited in claim 4, wherein the intermediate layer comprises a material selected from the group composed of Al, an alloy of Al, FeNi, FeCrNi and stainless steel, and that the first patterned metal layer and the second patterned metal layer contain copper.

6. The electronic device as recited in claim 1, wherein the intermediate layer is made from a material that can be selectively etched with respect to the first patterned metal layer.

7. The electronic device as recited in claim 6, wherein the intermediate layer is a metal.

8. The electronic device as recited in claim 7, wherein the intermediate layer comprises a material selected from the group composed of Al, an alloy of Al, FeNi, FeCrNi and stainless steel, and that the first patterned metal layer and the second patterned metal layer contain copper.

9. The electronic device as recited in claim 1, wherein the first electric element is a semiconductor element which is placed on the first side of the carrier with a flip-chip technique.

10. The electronic device as recited in claim 9, wherein connection conductors are defined in the second patterned metal layer and the corresponding etch mask, said connection conductors are laterally displaced with respect to contacts in the semiconductor element.

* * * * *